US011428659B2

(12) United States Patent
Wienecke

(10) Patent No.: US 11,428,659 B2
(45) Date of Patent: Aug. 30, 2022

(54) HYDROGEN SENSOR AND METHOD FOR ITS PRODUCTION, MEASURING DEVICE, AND METHOD FOR MEASURING A HYDROGEN CONCENTRATION

(71) Applicant: Materion GmbH, Wismar (DE)

(72) Inventor: Marion Wienecke, Wismar (DE)

(73) Assignee: Materion GmbH, Wismar (DE)

( * ) Notice: Subject to any disclaimer, the term of this patent is extended or adjusted under 35 U.S.C. 154(b) by 273 days.

(21) Appl. No.: 16/899,215

(22) Filed: Jun. 11, 2020

(65) Prior Publication Data
US 2020/0400599 A1 Dec. 24, 2020

(30) Foreign Application Priority Data
Jun. 21, 2019 (EP) ..................................... 19181581

(51) Int. Cl.
*G01N 27/12* (2006.01)
*G01N 33/00* (2006.01)

(52) U.S. Cl.
CPC ........... *G01N 27/125* (2013.01); *G01N 27/12* (2013.01); *G01N 27/122* (2013.01); *G01N 33/005* (2013.01)

(58) Field of Classification Search
CPC .. G01N 27/125; G01N 27/122; G01N 33/005; G01N 27/12
See application file for complete search history.

(56) References Cited

U.S. PATENT DOCUMENTS

| 3,479,257 A | 11/1969 | Shaver | |
| 5,670,115 A * | 9/1997 | Cheng | G01N 27/12 |
| | | | 204/291 |
| 7,340,941 B1 * | 3/2008 | Fruhberger | G01N 29/036 |
| | | | 73/24.01 |
| 7,791,150 B1 | 9/2010 | Seal et al. | |
| 2005/0258051 A1 * | 11/2005 | Ono | G01N 33/005 |
| | | | 427/125 |
| 2009/0084161 A1 | 4/2009 | Wienecke et al. | |

FOREIGN PATENT DOCUMENTS

| CN | 108872314 A | 11/2018 |
| DE | 10011164 A1 | 9/2001 |
| DE | 102006018767 A1 | 10/2007 |
| KR | 20180074100 A | 7/2018 |

OTHER PUBLICATIONS

Hongchuan Jiang et al., "Low Concentration Response Hydrogen Sensors Based on Wheatstone Bridge", Preprints.org, Feb. 25, 2019, p. 1-8, Creative Commons CC, USA.

* cited by examiner

*Primary Examiner* — Benjamin R Schmitt
(74) *Attorney, Agent, or Firm* — Rankin, Hill & Clark LLP

(57) ABSTRACT

The invention relates to a hydrogen sensor (8) and a method for its production, a measuring device (2), and a method for measuring a hydrogen concentration. The hydrogen sensor (8) for measuring a hydrogen concentration in an environment (4) includes a substrate (10) on which a hydrogen-absorbing sensor medium (14) is applied as a thin film in a sensor region (12) communicating with the environment. The sensor medium (14) changes its volume depending on a hydrogen concentration in the sensor medium (14), and said change of the volume causes a variation of a mechanical strain introduced by the sensor medium (14) in the substrate (10). In a preferred embodiment, the substrate (10) of the hydrogen sensor (8) is a piezoresistive semiconductor, at least within the sensor region (12).

19 Claims, 4 Drawing Sheets

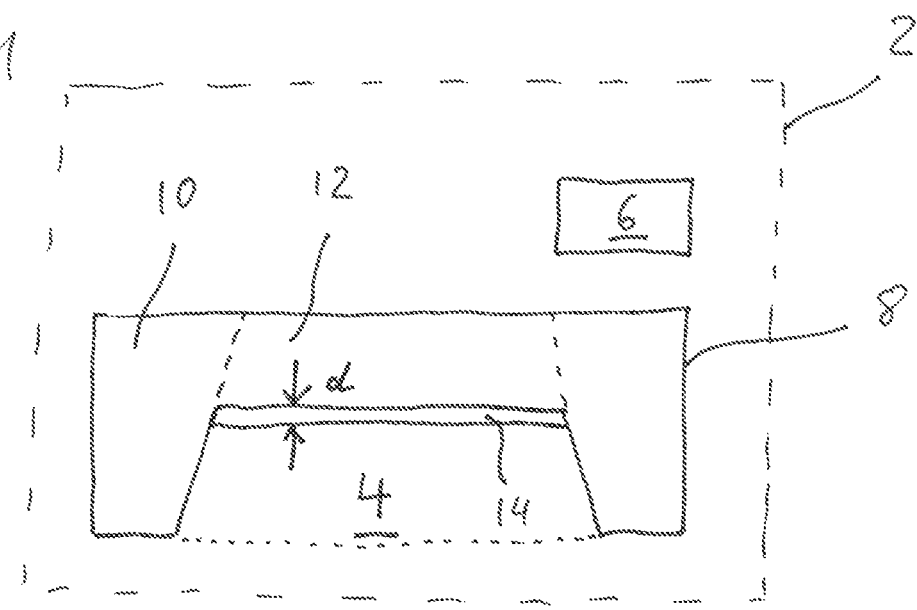
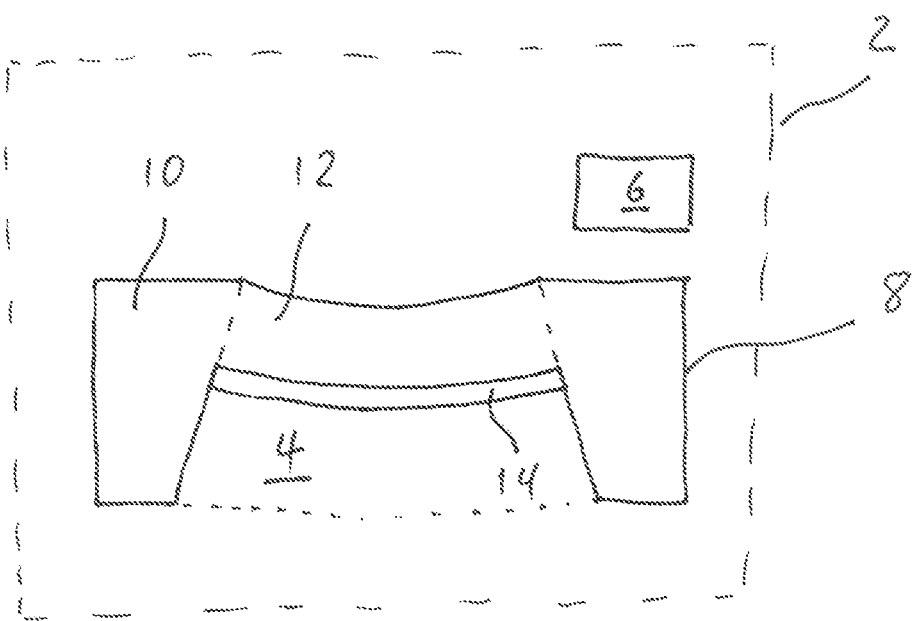

HYDROGEN SENSOR AND METHOD FOR ITS PRODUCTION, MEASURING DEVICE, AND METHOD FOR MEASURING A HYDROGEN CONCENTRATION

PRIORITY CLAIM

The present application claims priority to European Patent Application No. EP 19 181 581.0, filed Jun. 21, 2019.

BACKGROUND OF INVENTION

Field of Invention

The invention relates to a hydrogen sensor for measuring a hydrogen concentration in an environment, comprising a substrate on which a hydrogen-absorbing sensor medium is applied as a thin film in a sensor region communicating with the environment, wherein the sensor medium changes its volume depending on a hydrogen concentration in the sensor medium, and said change of the volume causes a variation of a mechanical strain introduced by the sensor medium in the substrate. Furthermore, the invention relates to a measuring device for measuring a hydrogen concentration in an environment, comprising a measuring unit and such a hydrogen sensor. Furthermore, the invention relates to a method for producing such a hydrogen sensor. Finally, the invention relates to a method for measuring a hydrogen concentration in an environment.

Brief Description of Related Art

Hydrogen sensors with which hydrogen concentrations can be measured in gases such as in air are known in different variants. The numerous commercially available hydrogen sensors are based on few physical effects, which are measurable. One of these physical effects is the capability of different materials to absorb hydrogen. Depending on the amount of hydrogen dissolved in the material used as a sensor, one or more of the measurable physical properties changes.

A hydrogen sensor in which a change in the optical properties of the sensor material is used is known from DE 10 2006 018 767 A1. With the sensor known from this document, a sensor medium is illuminated with electromagnetic radiation, and a transmission coefficient of the sensor medium is measured by means of a detector. A material is therefore used as the sensor medium, the transmission coefficient of which varies depending on the hydrogen concentration in a measuring environment of the sensor medium. The measured transmission coefficient is used as a measure for the hydrogen concentration in the environment.

In U.S. Pat. No. 7,791,150 B1, a hydrogen sensor is disclosed in which a structured electrode is applied on a silicon wafer which has a thermally-generated oxide layer on its top side. A hydrogen-sensitive semiconductor oxide film ($In_2O_3$ doped with $SnO_2$) is applied thereupon. This hydrogen-sensitive film is for example applied with a sol gel method. Moreover, a top side of this film is provided with a hydrogen-selective film. A change in the electrical properties of the semiconductor oxide film is used as a quantitative measure for the hydrogen concentration.

Another hydrogen sensor is known from KR 20180074100. A film system is provided which consists of a polymer film that serves as a substrate, an adhesion-promoting film or layer, and a palladium film applied thereupon. If the palladium film is exposed to a hydrogen-containing environment, the palladium film therefore changes its volume. This change in volume causes mechanical strain, which is build up in the above-described film system. The film system is designed as a bending bar. Moreover, the mechanical strain causes the bending bar to curve more or less strongly depending on the hydrogen concentration.

Another hydrogen sensor is known from CN 108872314 in which a film consisting of palladium is applied to zinc oxide (ZnO) as a basic material. The previously-described effect that palladium experiences a change in volume upon absorbing hydrogen is used by this sensor to exert a mechanical force on the zinc oxide. Since the zinc oxide shows a piezoelectric effect, a passive sensor can be provided. The piezoelectric strain on the zinc oxide is a direct measure for the hydrogen concentration to which the palladium film is exposed.

The switchable physical properties of palladium result from the interaction between the metal atoms and the hydrogen, which is solved in the metal at anatomic level at interstitials. Depending on the hydrogen concentration, i.e., the amount of hydrogen dissolved in the metal lattice, the lattice constant of palladium changes, which is associated with the volumetric expansion of the material. The effect is reversible.

BRIEF SUMMARY OF THE INVENTION

It is an object of the invention to provide an enhanced hydrogen sensor, an enhanced measuring device as well as an enhanced method for measuring a hydrogen concentration, and an enhanced method for producing such a hydrogen sensor.

The object is solved by a hydrogen sensor for measuring a hydrogen concentration in an environment, comprising a substrate on which a hydrogen-absorbing sensor medium is applied as a thin film in a sensor region communicating with the environment, wherein the sensor medium changes its volume depending on a hydrogen concentration in the sensor medium, and said change of the volume causes a variation of a mechanical strain introduced by the sensor medium in the substrate, wherein this hydrogen sensor is developed in that the substrate is a piezoresistive semiconductor, at least within the region of the sensor.

With the hydrogen sensor according to aspects of the invention, a large measuring range of hydrogen concentrations can be measured. In addition, the sensor does not have any cross-sensitivities to other gases and shows a fast reaction time. The sensor uses the volumetric change of the sensor medium due to hydrogen absorption. The sensor medium introduces variable mechanical strain, which means strain at different levels or intensities, into the substrate, the strain depending on the hydrogen concentration. Since the piezoresistive properties of the semiconductor are also used, the mechanical strain and therefore the hydrogen concentration can be measured easily and very precisely. Advantageously, the mechanical strain within the sensor region of the piezoresistive semiconductor can be measured electrically, for example by providing resistance structures on the semiconductor in the form of a Wheatstone bridge.

According to another embodiment, it is provided that the sensor medium is a metal or a metal alloy.

According to another embodiment, it is provided that the piezoresistive semiconductor is silicon. In other words, the substrate of the hydrogen sensor consists of silicon, at least in the sensor region.

Furthermore it is in particular provided that the sensor medium comprises palladium, yttrium, scandium, a lanthanide, an actinide, tungsten oxide and/or vanadium oxide.

According to another embodiment, it is provided that the sensor medium is a palladium alloy, or a mixture, alloy or compound consisting of one or more of the following materials: palladium, yttrium, scandium, a lanthanide, an actinide, tungsten oxide, and vanadium oxide.

According to another advantageous embodiment, it is provided that the sensor medium is an alloy consisting of palladium and gold ($Pd_xAu_y$ alloy), or an alloy consisting of palladium and nickel ($Pd_xNi_y$ alloy), wherein in particular the portion of gold or nickel lies between 0.5 at % and 50 at % ($Pd_{0.5}AU_{99.5}$ alloy to $Pd_{50}Au_{50}$ alloy, or $Pd_{0.5}Ni_{99.5}$ alloy to $Pd_{50}Ni_{50}$ alloy).

The sensor medium absorbs hydrogen, wherein the hydrogen atoms are incorporated in the atomic lattice of the sensor medium at interstitials. This applies in particular to the use of palladium or a palladium alloy as a sensor medium, as well as to all other cited materials.

During the incorporation of hydrogen atoms in the atomic lattice, different physical effects occur that are known per se. One of these effects that, however, is not specifically used by the hydrogen sensor according to the invention is the transition of the α-phase into the β-phase. This holds true when palladium or a palladium alloy is used as the sensor medium. Whereas the α-phase is metallically opaque, the β-phase of palladium is transparent, or at least more transparent than the α-phase. This phase transition can be used in order to optically measure a hydrogen concentration in the palladium used as the sensor medium. However, this has the technical disadvantage that the transition from the α-phase to the β-phase must occur before a measurement signal is available. The same holds true for a measurement that is based on the physical effect that the α-phase is metallically conductive, and the β-phase is semi-conductive. The phase transition must also occur in a sensor which uses this effect. For example, the α-phase in palladium exists up to a hydrogen concentration of 1.68 at %. This means that with such a sensor that uses the above-described phase transition, low hydrogen concentrations cannot be measured, or can only be measured with difficulties.

The above-outlined technical disadvantages are advantageously overcome with the sensor according to aspects of the invention. While for example the palladium is in the α-phase, i.e., given low hydrogen concentrations, a change in the volume of the sensor medium occurs from the hydrogen atoms incorporated at the interstitials. This change in the volume that is associated with a change in the lattice constant causes the sensor film to expose mechanical strain on the substrate. This strain can be measured using the piezoresistive effect in the substrate. With the sensor according to aspects of the invention, it is therefore possible to detect low hydrogen concentrations with great precision.

The above-explained physical and technical effects will be explained only using palladium as an example. They also occur with greater or smaller effect in the other mentioned materials.

The hydrogen sensor is advantageously further developed in that the sensor medium configured as a thin film has a film thickness that is less than 500 nm and in particular the film thickness is between 5 nm and 100 nm, and furthermore in particular film thickness is between 5 nm and 20 nm.

The aforementioned film thicknesses have proven to be advantageous in practice. On the one hand, a sufficiently large mechanical strain can be generated with a sensor film that has a film thickness within the indicated ranges so that a measurable effect occurs within the sensor range of the substrate. On the other hand, the effort for producing the film is manageable. Delamination of the applied sensor film does not occur as it is frequently observable for large film thicknesses.

Furthermore, the hydrogen sensor according to another embodiment is further developed in that the sensor medium is a thin film made by means of sputter deposition.

Alternatively to sputter deposition, which is preferably production by means of DC magnetron sputter deposition, other thin film techniques can be used such as physical vapor deposition, laser deposition, etc.

According to another embodiment, the hydrogen sensor is further developed in that a cover film is present on top of the sensor medium. The cover film is provided on a surface of the sensor medium that would be in contact with the environment without a cover film. The cover film is permeable to hydrogen. For example, the cover film can be a $SiO_2$ film made by CVD (chemical vapor deposition). The cover film can serve as a protective film against aggressive components in the environment. It can also be used to harmonize the elastomechanical properties of the substrate and the hydrogen-absorbing film consisting of the sensor medium with each other.

Furthermore, the object is solved by a measuring device for measuring a hydrogen concentration in an environment, comprising a measuring unit, wherein the measuring device is developed by a hydrogen sensor according to one or more of the aforementioned embodiments, the sensor medium of which communicates with the environment, wherein the measuring unit is configured to measure an ohmic resistance of the substrate, in particular an ohmic resistance of the substrate within the sensor region, and to determine a hydrogen concentration in the environment from the value of the measured ohmic resistance.

In fact, mechanical strain introduced into the substrate by the sensor film is inferred in such a measuring device using the ohmic resistance of resistances or their difference formed or existing in the sensor region in the substrate, for example using a Wheatstone bridge circuit. An expansion/change in volume of the sensor film that causes the mechanical strain can be inferred from the value of the mechanical strain. This change in volume in turn directly correlates with the amount of hydrogen absorbed by the sensor medium. Under the valid assumption that the concentration of hydrogen in the sensor medium is in equilibrium with the environment in which the hydrogen concentration is measured, the hydrogen concentration existing in this environment can be directly inferred using the measured ohmic resistance.

Moreover, same or similar advantages apply to the measuring device as have been already mentioned above with respect to the hydrogen sensor.

The object is furthermore solved by a method for producing a hydrogen sensor according to one or more of the aforementioned embodiments, wherein this method is developed in that the sensor medium is deposited on the substrate as a thin film by means of sputter deposition, in particular by means of magnetron sputter deposition or by physical vapor deposition.

The production of the sensor layer by means of sputter deposition has proven to be a highly efficient method.

The object is also solved by a method for measuring a hydrogen concentration in an environment that is developed by the following steps:

exposing a hydrogen-absorbing sensor medium to the environment, wherein the sensor medium is applied as a thin film in a sensor region of a substrate, and the substrate is a piezoresistive semiconductor, at least within the sensor region, measuring an ohmic resistance of the substrate, in particular an ohmic resistance of the substrate within the sensor region, and determining a hydrogen concentration in the environment from the value of the measured ohmic resistance.

Same or similar advantages as those already mentioned with respect to the hydrogen sensor also apply to the method for measuring the hydrogen concentration.

According to other embodiments, a material is used as the piezoresistive semiconductor whose k-value≥2, in particular ≥5, furthermore in particular ≥10, and also furthermore in particular ≥25. Within the context of the present specification, it is understood the k-value is the proportionality factor between a quotient consisting of an expansion-related change in length from the initial length and an expansion-related change in resistance from the initial resistance on a resistance measuring path of the semiconductor. This relationship is also described by the equation below:

$$\Delta R/R = k * \Delta L/L$$

In the aforementioned equation, R is the ohmic resistance of the piezoresistive semiconductor in the sensor region measured along length L. ΔR is the change of ohmic resistance which is caused by the change in length ΔL. The change in length ΔL is a consequence of the deformation of the substrate in the sensor region as a consequence of the mechanical strain introduced into this region by the sensor medium.

Further features of the invention will become apparent from the description of the embodiments according to the invention together with the claims and the accompanying drawings. Embodiments according to the invention can fulfill individual features or a combination of several features.

Within the scope of the invention, features which are designated by "in particular" or "preferably" are understood to be optional features.

BRIEF DESCRIPTION OF THE DRAWINGS

The invention is described below, without restricting the general idea of the invention, based on exemplary embodiments in reference to the drawings, whereby we expressly refer to the drawings with regard to all details according to the invention that are not explained in greater detail in the text. In the figures:

FIG. 1 shows a measuring device having a hydrogen sensor in a schematically simplified cross-sectional view, wherein the sensor medium is not exposed to a concentration of hydrogen, FIG. 2 shows this measuring device, also in a schematically simplified cross-sectional view, wherein the sensor medium is exposed to a concentration of hydrogen.

In the drawings, the same or similar elements and/or parts are provided with the same reference numbers in each case; a reintroduction will therefore always be omitted.

DETAILED DESCRIPTION OF AN EMBODIMENT OF THE INVENTION

Figure 3:
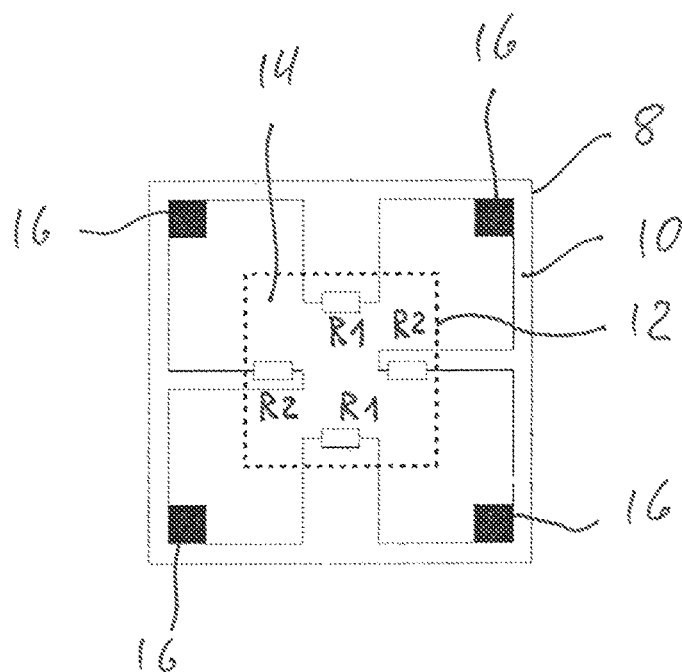
FIG. 3 shows a schematically simplified plan view of a hydrogen sensor.

In a schematically simplified cross-sectional view, FIG. 1 shows a measuring device 2 for measuring a hydrogen concentration in an environment 4. The environment 4 is in contact via channels, connections, etc. with another environment or atmosphere in which a hydrogen concentration is to be measured. To this end, suitable measures are taken to close off the environment 4 in the measuring device 2 and to couple it via connections to the other measuring environment. The measuring device 2 furthermore comprises a measuring unit 6 which is for example a computer, a microcontroller, or suitable software means implemented in another unit. The measuring unit is configured to measure an ohmic resistance, and in this regard comprises for example inter alia a voltage source and a voltage measuring device. The measuring device 2 furthermore comprises a hydrogen sensor 8 that is configured to measure the hydrogen concentration in the environment 4. The hydrogen sensor 8 comprises a substrate 10 on which a hydrogen-absorbing sensor medium 14 is applied as a thin film in a sensor region 12 communicating with the environment 4.

By way of an example only, the environment 4 is arranged on a bottom side of the sensor region 12. It is also provided that the sensor medium 14 is applied as a thin film onto a top side of the sensor region 12, and the environment 4 in which the hydrogen concentration is measured is accordingly located on the top side. It is however necessarily provided that the sensor film 14 is only located on one side of the sensor region 12 configured for example as a silicon membrane, and this side, i.e., the sensor film, communicates with the hydrogen-containing environment 4.

The sensor medium 14 is for example a metal or a metal alloy. The sensor medium 14 is for example a thin film comprising palladium, yttrium, scandium, a lanthanide, an actinide, tungsten oxide or vanadium oxide, wherein alloys and mixtures of these materials are also provided. In particular, it is provided that the sensor medium 14 is an alloy consisting of palladium and gold (PdAu), or consisting of palladium and nickel (PdNi) that is produced by co-sputtering deposition. To accomplish this, the substrate 10 is introduced into the receivers of a sputtering system, and the PdAu or PdNi film is applied directly onto the substrate 10.

The film thickness d of the sensor medium 14 applied as a thin film onto the substrate 10 is for example less than 500 nm; it is furthermore for example between 5 nm and 100 nm, and furthermore for example between 5 nm and 20 nm.

The sensor medium 14 is a material that changes its volume depending on a hydrogen concentration present in the sensor medium 14. This variation of the volume changes the mechanical strain introduced by the sensor medium 14 into the substrate 10 in the sensor region 12. A comparison between FIGS. 1 and 2 shows this effect.

FIG. 2 shows the measuring device 2, also in a schematically simplified cross-sectional view, wherein the sensor medium 14 is exposed to a concentration of hydrogen existing in the environment 4. This means that the sensor medium 14 expands, and this expansion leads to the schematic bending of the substrate 10 in the sensor region 12 which is shown exaggerated for reasons of clarity. If the sensor medium 14 is located on the opposite top side of the substrate 10, it will bend in the opposite direction. The substrate 10 is a piezoresistive semiconductor, at least in the sensor region 12. The mechanical strain arising in the sensor medium 14 also cause the substrate 10 to be exposed to mechanical strain, at least in the sensor region 12. These mechanical strain can be detected by the measuring unit 6 by using the piezoresistive effect. To accomplish this, the measuring unit 6 contacts the substrate 10 by electrical connections not shown in the figures.

The measuring unit 6 measures the ohmic resistance, or respectively a change in the ohmic resistance of the substrate 10, at least in the sensor region 12. A hydrogen concentration in the environment 4 can be inferred from the value of the measured ohmic resistance.

FIG. 3 shows a schematically simplified plan view of a hydrogen sensor 8. As an example, FIG. 3 shows a plan view of the side of a substrate 10 of the hydrogen sensor 8 on which the sensor medium 14 is applied in the sensor region 12. The substrate 10 comprises contact pads 16 by which the hydrogen sensor 8 contacts the measuring unit 6. By means of the contact pads 16, it is possible to determine changes in the resistances R1, R2 which are connected in the form of a Wheatstone bridge circuit.

Figure 4:
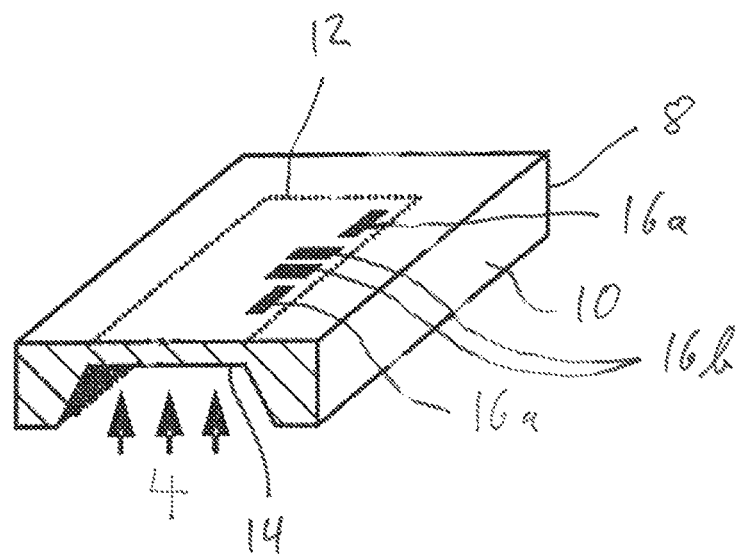
FIG. 4 shows a schematically simplified perspective view of another hydrogen sensor.

FIG. 4 shows a schematically simplified perspective view of another hydrogen sensor 8. Within a sensor region 12, this comprises a sensor medium 14 applied from the bottom side which, as indicated by arrows, is exposed to a hydrogen-containing environment 4. The mechanical strain caused by the sensor medium 14 are detected with the assistance of resistance measurements, wherein tapping occurs at the contact pads 16 by which an ohmic resistance of the substrate 10 can be measured in the sensor region 12. Again, circuitry can for example be in the form of a Wheatstone bridge circuit. In so doing, the resistance between the contact pads 16a is measured as resistance R2, and the resistance between the contact pads 16b is measured as resistance R1.

Figure 5:
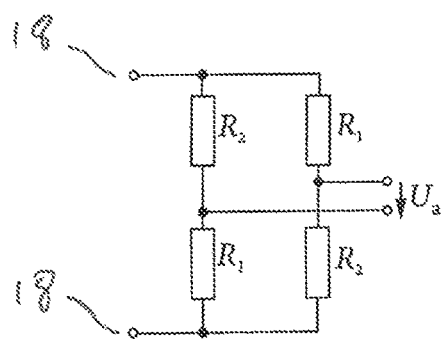
FIG. 5 shows a simplified circuit diagram of the circuitry of the resistances measured within the sensor region of the piezoresistive semiconductor that are connected in the form of a Wheatstone bridge circuit.

FIG. 5 shows a schematically simplified circuit diagram of the circuitry of the ohmic resistances R1 and R2, measured for example within the sensor region 12 of the piezoresistive semiconductor, that are connected in the form of a Wheatstone bridge circuit. A voltage is applied to the two terminals 18, and the diagonal voltage or bridge voltage Ua of the resistances R1, R2 connected as a voltage divider are measured. A change in the bridge voltage Ua is a measure of the change in the resistances R1, R2, and is therefore a direct measure of the mechanical strain introduced by the sensor medium 14 into the substrate 10 in the sensor region 12. Accordingly, the hydrogen concentration in the environment 4 can be directly read from the bridge voltage Ua.

Figure 6:
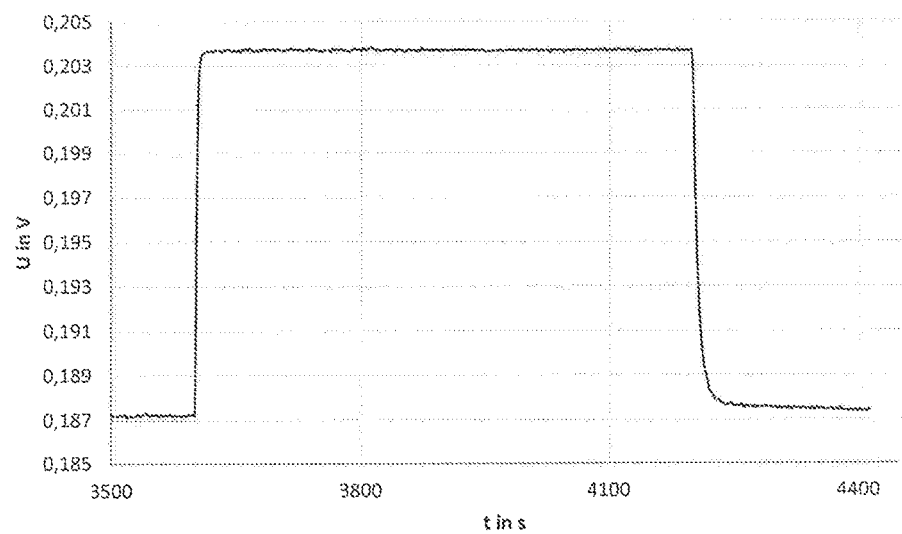
FIGS. 6 to 8 show examples of measurements of different hydrogen concentrations in an environment depending on the time, performed using a hydrogen sensor according to aspects of the invention.
Figure 7:
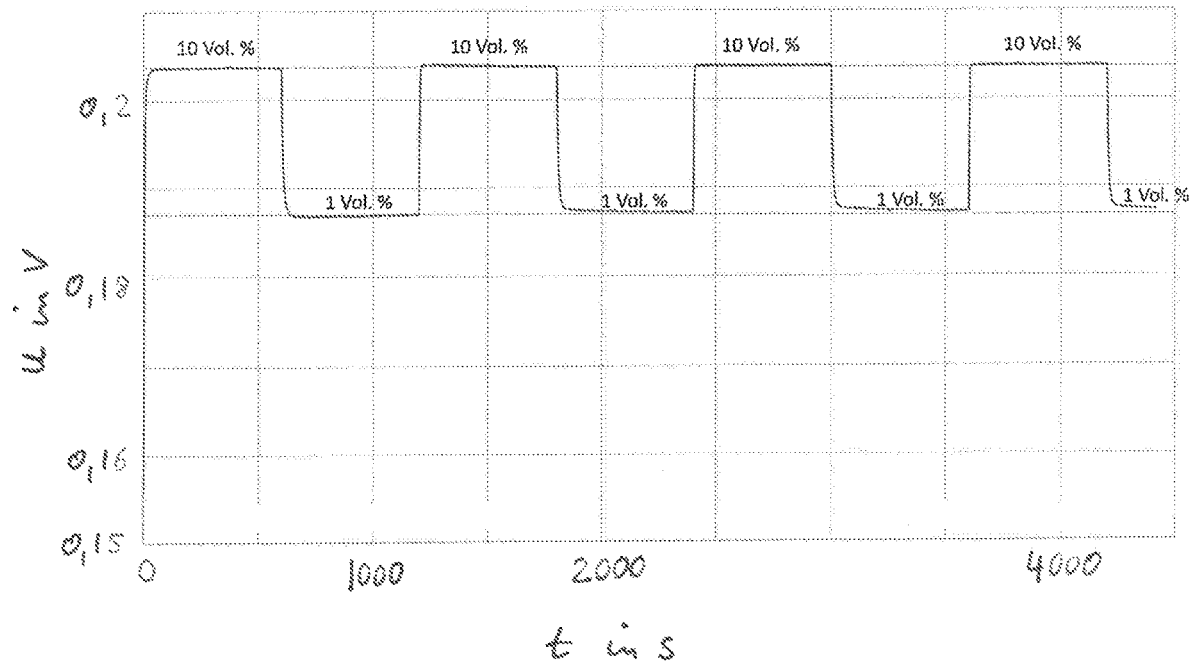
Figure 8:
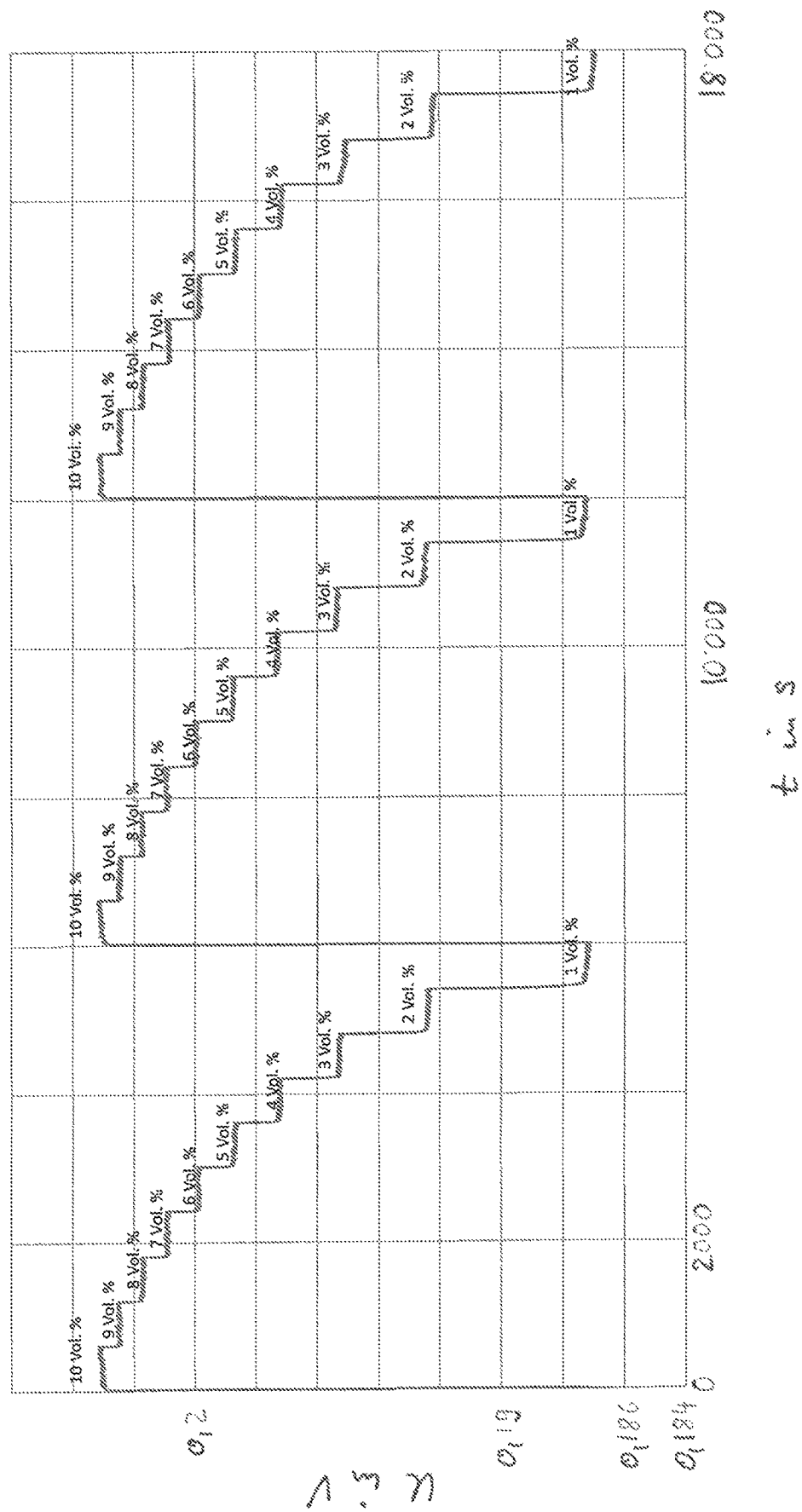

FIGS. 6 to 8 show examples of measurements of different hydrogen concentrations in the environment 4 depending on time t. The electrical voltage is indicated in volts on the vertical axis, whereas the horizontal axis shows the time t in seconds. The electrical voltage shown on the vertical axis is a direct measure of the mechanical strain predominating in the sensor region 12 and is therefore also a direct measure of the hydrogen concentration in the environment 4. It can clearly be seen that the hydrogen sensor 8 supplies very constant measuring results within a large measuring range. In FIG. 6, the measurement starts at a concentration of 1 vol % hydrogen in air and increases to 10 vol %. In the measurement shown in FIG. 7, concentrations of 1 vol % hydrogen in air and 10 vol % are also measured. The measurements in FIGS. 6 and 7 were each carried out for a maximum duration of 4400 sec. which corresponds to 73 min. FIG. 8 shows another measurement in which hydrogen concentrations were measured between 1 vol % and 10 vol %. The hydrogen sensor 8 manifests a high sensitivity, fast response behavior (FIG. 6), a stable measured value over time (FIG. 6) and measuring results that are largely reproducible (FIGS. 7 and 8).

All mentioned features, including those taken from the drawings by themselves as well as individual features which are disclosed in combination with other features, are considered essential to the invention by themselves and in combination. Embodiments according to the invention can be fulfilled by individual features or a combination of several features.

LIST OF REFERENCE SIGNS

2 Measuring device
4 Environment
6 Measuring unit
8 Hydrogen sensor
10 Substrate
12 Sensor region
14 Sensor medium
16, 16a, 16b Contact pads
18 Terminal
d Film thickness
R1, R2 Resistances
Ua Bridge voltage

What is claimed is:

1. A hydrogen sensor for measuring a hydrogen concentration in an environment, the hydrogen sensor comprising a substrate on which a hydrogen-absorbing sensor medium is applied as a thin film in a sensor region communicating with the environment, wherein the sensor medium changes its volume depending on a hydrogen concentration in the sensor medium, and said change of the volume causes a variation of a mechanical strain introduced by the sensor medium in the substrate, and wherein the substrate is a piezoresistive semiconductor, at least within the sensor region.

2. The hydrogen sensor according to claim 1, wherein the sensor medium is a metal or a metal alloy.

3. The hydrogen sensor according to claim 1, wherein the sensor medium comprises one or more of palladium, yttrium, scandium, a lanthanide, an actinide, tungsten oxide and vanadium oxide.

4. The hydrogen sensor according to claim 1, wherein the sensor medium is a palladium alloy, or a mixture, alloy or compound consisting of one or more of the following materials: palladium, yttrium, scandium, a lanthanide, an actinide, tungsten oxide, and vanadium oxide.

5. The hydrogen sensor according to claim 1, wherein the sensor medium is an alloy consisting of palladium and gold (PdxAuy alloy).

6. The hydrogen sensor according to claim 5, wherein the portion of gold lies between 0.5 at % and 50 at % (Pd0.5Au99.5 alloy to Pd50Au50 alloy).

7. The hydrogen sensor according to claim 1, wherein the sensor medium is an alloy consisting of palladium and nickel (PdxNiy alloy).

8. The hydrogen sensor according to claim 7, wherein the portion of nickel lies between 0.5 at % and 50 at % (Pd0.5Ni99.5 alloy to Pd50Ni50 alloy).

9. The hydrogen sensor according to claim 1, wherein the sensor medium is a thin film having a film thickness (d) that is less than 500 nm.

10. The hydrogen sensor according to claim 9, wherein the film thickness (d) is between 5 nm and 100 nm.

11. The hydrogen sensor according to claim 9, wherein the film thickness (d) is between 5 nm and 20 nm.

12. The hydrogen sensor according to claim 1, wherein the sensor medium is a thin film made by sputter deposition.

13. A measuring device for measuring a hydrogen concentration in an environment, the measuring device comprising a the measuring unit including the hydrogen sensor according to claim 1, wherein the sensor medium of the hydrogen sensor communicates with the environment, wherein the measuring unit is configured to measure an ohmic resistance of the substrate, and to determine the hydrogen concentration in the environment from the value of the measured ohmic resistance.

14. The measuring device according to claim 13, wherein the measuring unit is configured to measure the ohmic resistance of the substrate within the sensor region.

15. A method for producing a hydrogen sensor according to claim 1, the method comprising depositing the sensor medium on the substrate as a thin film by means of sputter deposition.

16. The method according to claim 15, wherein the sensor medium is deposited on the substrate as the thin film by means of magnetron sputter deposition.

17. The method according to claim 15, wherein the sensor medium is deposited on the substrate as the thin film by means of physical vapor deposition.

18. A method for measuring a hydrogen concentration in an environment, the method comprising steps of:
exposing a hydrogen-absorbing sensor medium to the environment, wherein the sensor medium is applied as a thin film in a sensor region of a substrate, and the substrate is a piezoresistive semiconductor, at least within the sensor region, wherein the sensor medium changes its volume depending on a hydrogen concentration in the sensor medium, and said change of the volume causes a variation of a mechanical strain introduced by the sensor medium in the substrate,
measuring an ohmic resistance of the substrate, and
determining a hydrogen concentration in the environment from the value of the measured ohmic resistance.

19. The method according to claim 18, wherein the ohmic resistance of the substrate is measured within the sensor region.

* * * * *